United States Patent
Pratt

(10) Patent No.: US 6,457,486 B1
(45) Date of Patent: Oct. 1, 2002

(54) BAILER HAVING LEAK-INHIBITING SEAL

(76) Inventor: David W. Pratt, 13512 Feather Sound Cir. West, Apt 1401, Clearwater, FL (US) 33762

( * ) Notice: Subject to any disclaimer, the term of this patent is extended or adjusted under 35 U.S.C. 154(b) by 0 days.

(21) Appl. No.: 10/063,418

(22) Filed: Apr. 22, 2002

Related U.S. Application Data

(62) Division of application No. 09/682,497, filed on Sep. 7, 2001, now Pat. No. 6,390,123.

(51) Int. Cl.[7] ............................. F16K 15/06; G01N 1/12
(52) U.S. Cl. ................................ 137/533.21; 137/546
(58) Field of Search ................. 137/533.11, 533.17, 137/533.19, 533.21, 533.31, 546; 166/264; 294/68.22, 68.25; 73/864.63

(56) References Cited

U.S. PATENT DOCUMENTS

| | | | | |
|---|---|---|---|---|
| 1,210,487 A | * | 1/1917 | Kaul | ........................ 73/864.63 |
| 2,678,563 A | * | 5/1954 | Parrish | ..................... 73/864.65 |
| 6,135,523 A | * | 10/2000 | Pratt | ..................... 137/533.21 |

* cited by examiner

*Primary Examiner*—John Rivell
*Assistant Examiner*—Ramesh Krishnamurthy
(74) *Attorney, Agent, or Firm*—Ronald E. Smith; Smith & Hopen, PA

(57) ABSTRACT

A substantially leak-free bailer includes an improved valve assembly at its lowermost end. A valve body is mounted to the lowermost end of a valve stem and the valve stem is slideably received within and guided by a central bore formed on a support member that spans the hollow interior of the bailer at its lowermost end. The valve body may be hemispherical, frusto-conical, or elongate and downwardly tapered. The valve seat is configured to match the contour of the valve body. An annular ridge circumscribes the valve seat and serves as a barrier to particulate matter so that the valve body sits in the valve seat without interference from such particulate matter.

3 Claims, 6 Drawing Sheets

BAILER HAVING LEAK-INHIBITING SEAL

RELATED U.S. APPLICATION DATA

Divisional of application Ser. No. 09/682,497, filed on Sep. 7, 2001, now U.S. Pat. No. 6,390,123 B1.

BACKGROUND OF INVENTION

1. Field of the Invention

This invention relates, generally, to bailers. More particularly, it relates to a bailer having a valve assembly at its lower end that seals effectively against leakage when seated.

2. Description of the Prior Art

Bailers are elongate cylindrical tubes that are lowered into containers for liquid fluids, bodies of water, and the like for the purpose of taking a sample of the liquid fluid so that laboratory tests can be performed thereon.

In the industry standard bailer, a free-floating ball valve at the lower end of the bailer unseats from its valve seat when the bailer is lowered into a liquid fluid, i.e., as liquid fluid flows upwardly into the hollow interior of the bailer. The ball valve travels downwardly into seating relation to its valve seat when the bailer is lifted upwardly from the liquid fluid. When properly seated, the ball valve should substantially prevent leakage of the liquid fluid from the hollow interior of the bailer.

In practice, however, the ball valve leaks profusely. The clothing of the person carrying the bailer to a vehicle that will transport the collected sample to a lab often gets wet as the liquid fluid within the bailer leaks part the ball valve. If the liquid fluid is an acid or other irritant, the leakage is more than a mere nuisance. Even if the liquid fluid is just water, the loss of sample is undesirable.

The seat for the ball valve is an annular step formed on an interior surface of a frusto-conical wall that defines the lowermost end of the bailer. A single grain of sand on the annular step can defeat proper seating of the ball valve. Sand and other particles are commonly found in the liquid fluids that are collected by bailers in the field.

What is needed, then, is an improved valve assembly at the lowermost end of a bailer. The improved valve would not be defeated by a single grain of sand and would not be rendered ineffective by even relatively large amounts of sand.

However, it was not obvious to those of ordinary skill in this art how a leak-inhibiting valve assembly could be provided, in view of the art considered as a whole at the time the present invention was made.

SUMMARY OF INVENTION

The long-standing but heretofore unfulfilled need for an innovation that overcomes the limitations of the prior art is now met by a new, useful, and non-obvious invention. The present invention includes a substantially leak-free valve assembly for admitting liquid fluid into the hollow interior of a bailer as the bailer is lowered into a liquid fluid and for retaining liquid fluid within the hollow interior when the bailer is lifted from the liquid fluid.

A support means in the form of a spider member spans a hollow interior of the bailer near its lowermost end. A central bore is formed in the spider and has an axis of symmetry that is substantially coincident with a longitudinal axis of symmetry of the bailer.

The bailer is of the type that has a cylindrical main body, frusto-conical sidewalls at the lowermost end of the main body, and a cylindrical downspout at the lowermost end of the frusto-conical sidewalls.

A hemispherical-in-configuration valve body is secured to a lowermost end of a straight valve stem. The valve stem is slideably received within the central bore formed in the spider so that the hemispherical valve body rises and falls as liquid fluid flows into and out of the hollow interior of the bailer, respectively. The valve stem and the central bore cooperate to maintain the hemispherical valve body in substantial coincidence with the longitudinal axis of symmetry of the bailer as the hemispherical valve body rises and falls.

An annular concavity is formed in an interior surface of the frusto-conical sidewalls. It is configured to substantially match an exterior surface of the hemispherical valve body so that substantially no leakage of liquid fluid from the hollow interior of the bailer occurs when the hemispherical valve body is seated against the annular concavity.

In a variation of the first embodiment, an annular ridge of predetermined height is formed on the interior surface of the frusto-conical sidewalls. The annular ridge is integrally formed with the annular concavity and is adapted to provide a barrier to passage to at least one grain of particulate matter so that the at least one grain of particulate matter does not interfere with seating of the hemispherical valve body against the annular concavity.

In a second embodiment, the valve body and its matching valve seat are frustoconical in configuration, and a variation of the second embodiment includes the particle barrier of the first embodiment.

In a third embodiment, the valve body and its matching valve seat are downwardly tapered to form an elongate, narrow slot. A variation of the third embodiment includes a particle barrier formed in the downwardly-tapered sidewalls of the valve seat.

It is a primary object of this invention to advance the art of bailers by providing a bailer that is substantially leak-free.

A more specific object is to provide an improved valve structure for bailers.

Another major object is to provide a valve assembly that is not defeated by particulate matter that may be present in the liquid fluid collected by the bailer.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

Figure 1:
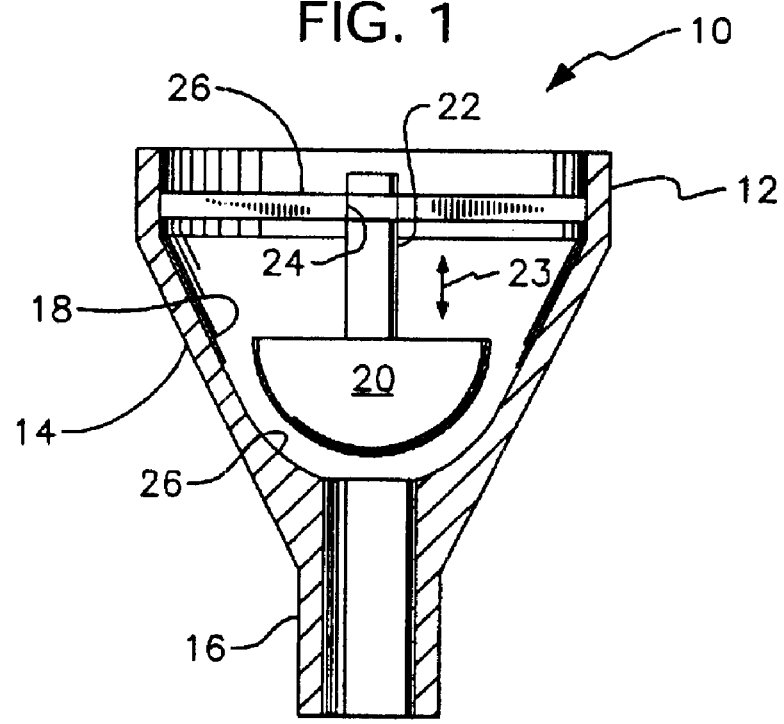
FIG. 1 is a side elevational, sectional view of a first embodiment of an improved valve means for a bailer.

Referring now to FIG. 1, it will there be seen that an exemplary embodiment of the invention is denoted as a whole by the reference numeral 10. It should be understood that only the lowermost end of a bailer is depicted.

The cylindrical sidewalls of bailer 10 are denoted 12. These sidewalls typically extend several feet in length, depending upon the application, and define the hollow interior of the bailer that receives the liquid fluid as it flows upwardly past a ball valve means and which contains the collected fluid when the ball valve is seated on its valve seat.

Tapered sidewalls 14 have a frusto-conical configuration. They extend from the lowermost end of cylindrical sidewalls 12 to the uppermost end of truncate cylindrical sidewalls 16 that form a downspout means at the lowermost end of the bailer. These tapered sidewalls 14 are provided in industry standard bailers. An annular step, not shown, is formed on interior surface 18 thereof about mid-length of sidewalls 14 and serves as the valve seat for a free-floating ball, not shown, when the bailer is lifted from the body of liquid fluid being sampled.

The unillustrated annular step of the prior art forms no part of this invention. Nor does any embodiment of this invention require the use of a free-floating ball, although such use is within the scope of this invention.

Figure 2:
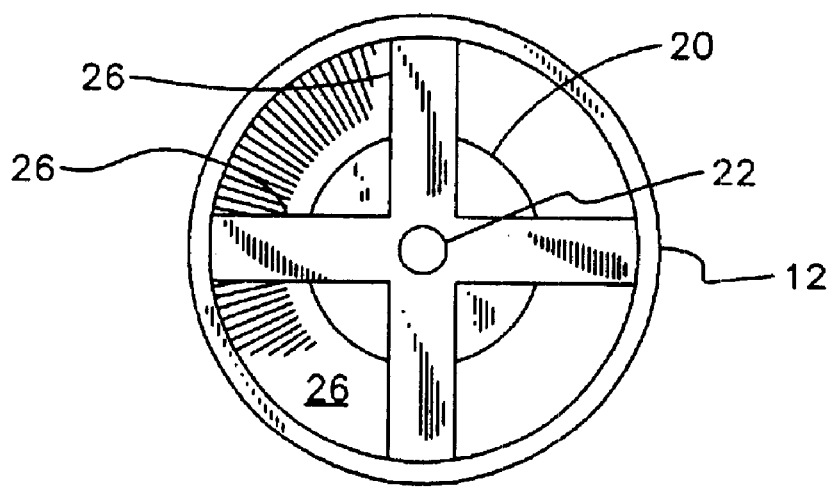
FIG. 2 is a bottom plan view of said first embodiment.

In the first embodiment, a hemispherical ball 20 is mounted at the lowermost end of a stem 22. Stem 22 is slideably received within a bore 24 formed in a support means that may take the form of spider 26 which spans the hollow interior of the bailer at the lowermost end of cylindrical sidewalls 12, as perhaps best understood in connection with FIG. 2. Spider 26 could have any number of radiating legs, and the invention is not limited to a spider having four legs as depicted.

Stem 22 slides up and down within bore 24 as liquid fluid flows into and out of the hollow interior of the bailer, respectively, as indicated by double-headed directional arrow 23 in FIG. 1. Hemispherical ball 20 thus rises and falls as well, guided by the stem and spider support assembly.

Bore 24 is formed in the center of spider 26, and the center or axis of symmetry of said bore is substantially coincident with the longitudinal axis of symmetry of the bailer.

A valve seat in the form of an annular concavity 26 is formed in the lowermost end of the interior surface 18 of tapered sidewalls 14. Its curvature matches the curvature of the exterior surface of hemispherical ball 20 so that a substantially perfect seal is formed when ball 20 is seated thereagainst.

Figure 3:
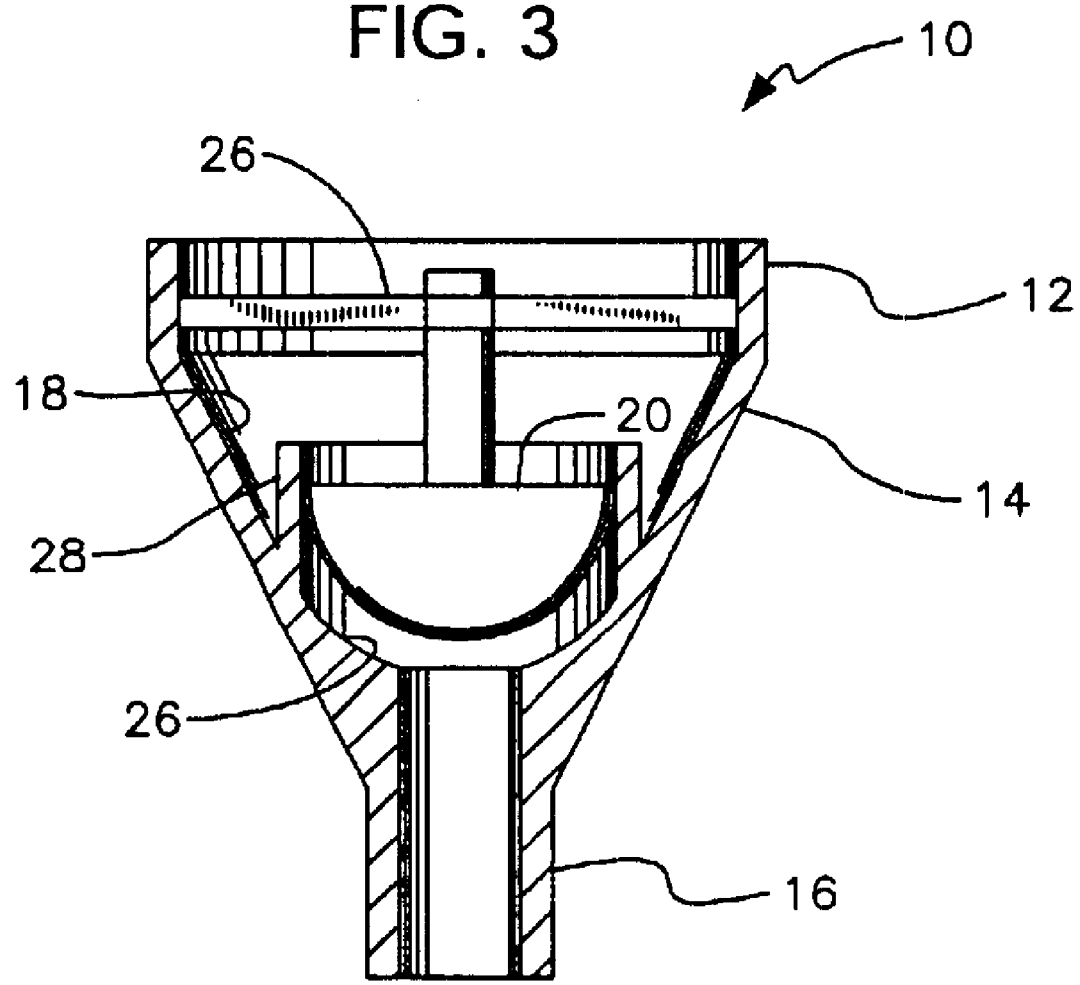
FIG. 3 is a side elevational, sectional view of an alternative embodiment of said first embodiment.

In the alternative embodiment of FIG. 3, annular ridge 28 is formed in concavity 26 near the lowermost end thereof, i.e., just slightly above downspout 16. The height of annular ridge 28 is preselected so that it provides an imperforate barrier to many grains of sand or other particles. In this way, neither a single grain of sand nor multiple grains of sand or other particulate debris can prevent seating of hemispherical ball 20 in complementally-formed valve seat 26. Sand or other particulate debris naturally accumulates behind annular ridge 28 as liquid fluid flows out of the hollow interior of the bailer in the moments before hemispherical ball 20 is seated against concave valve seat 26. In the prior art bailers mentioned above, such particulate debris collects on the annular step that circumscribes tapered walls 18 and prevents sealing of a free-floating ball thereagainst.

Figure 4:
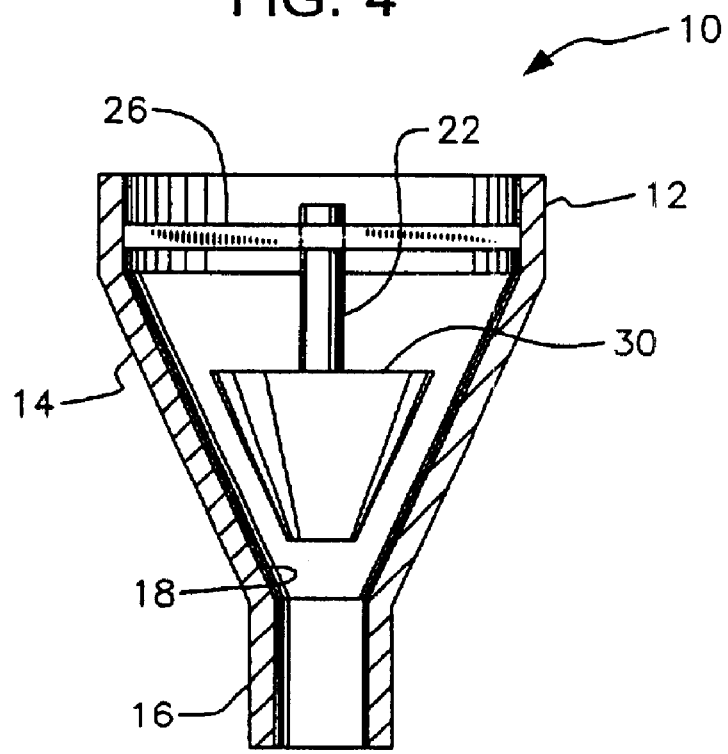
FIG. 4 is a side elevational, sectional view of a second embodiment of an improved valve means for a bailer.
Figure 5:
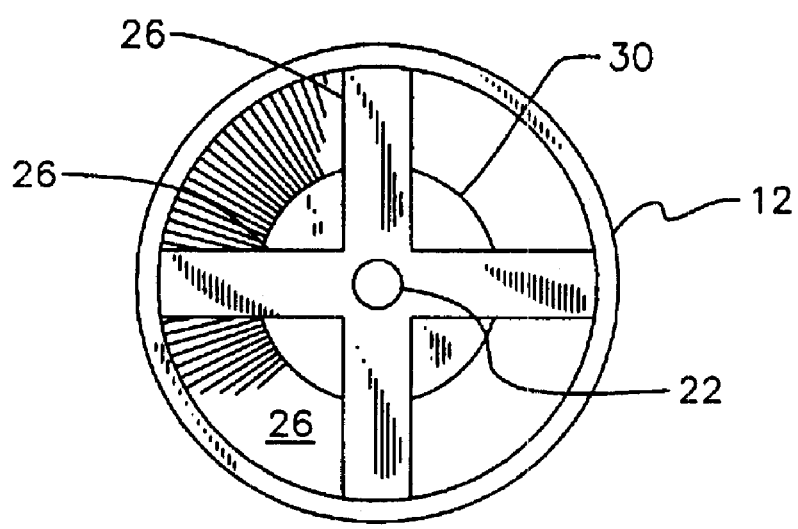
FIG. 5 is a bottom plan view of said second embodiment.
Figure 6:
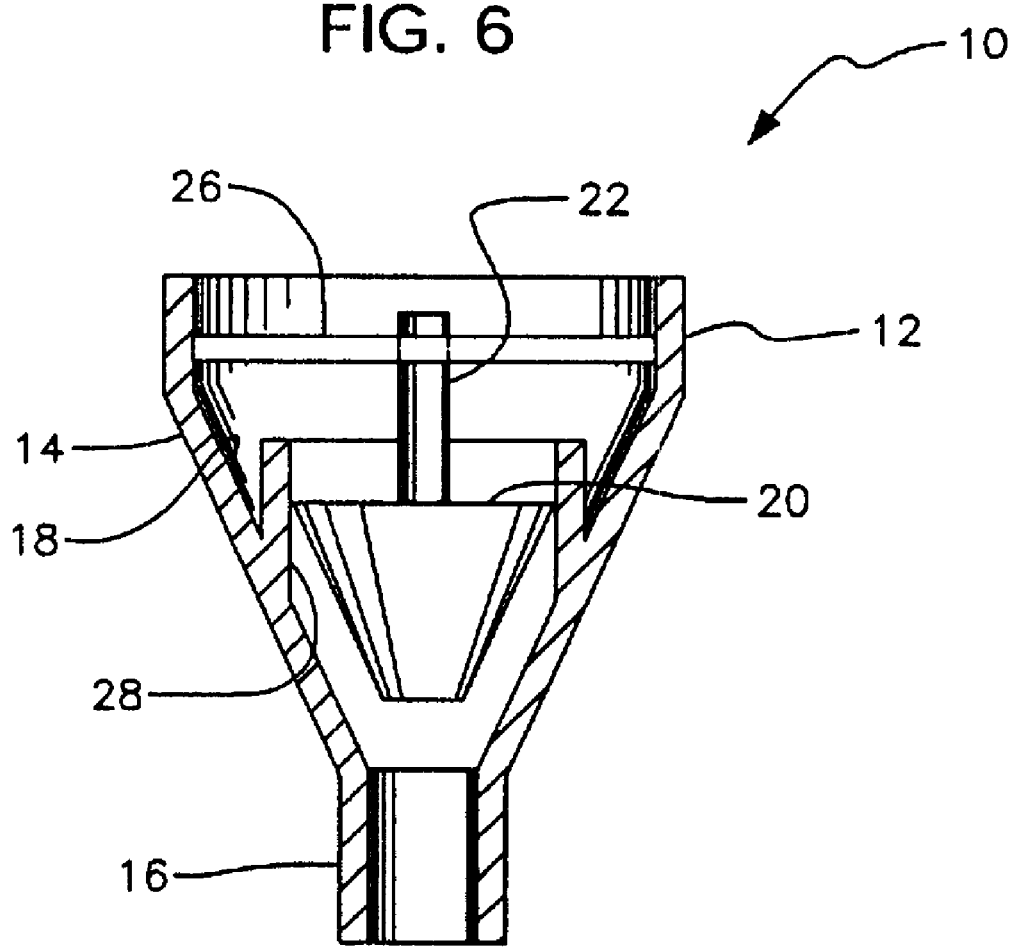
FIG. 6 is a side elevational, sectional view of an alternative embodiment of said second embodiment.

FIGS. 4 and 5 depict a second embodiment of the invention and FIG. 6 depicts a variation thereof. In the embodiments of FIGS. 4 and 5, frusto-conical valve body 30 seats against the flat interior surface of frusto-conical sidewalls 18 when liquid fluid flows out of the bailer, there being no ridge formed in said flat sidewalls. The embodiment of FIG. 6 adds annular ridge 28 as in the embodiment of FIG. 3. Downspout 16 is cylindrical as in the first embodiment.

Figure 7:
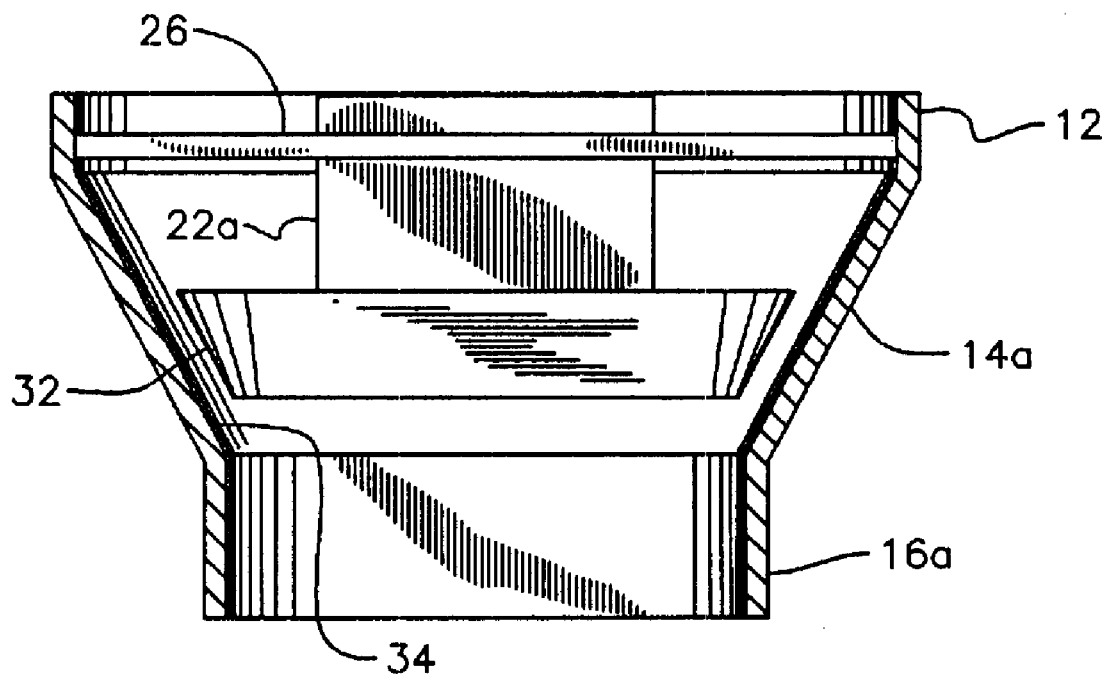
FIG. 7 is a side elevational, sectional view of a third embodiment of an improved valve means for a bailer.
Figure 8:
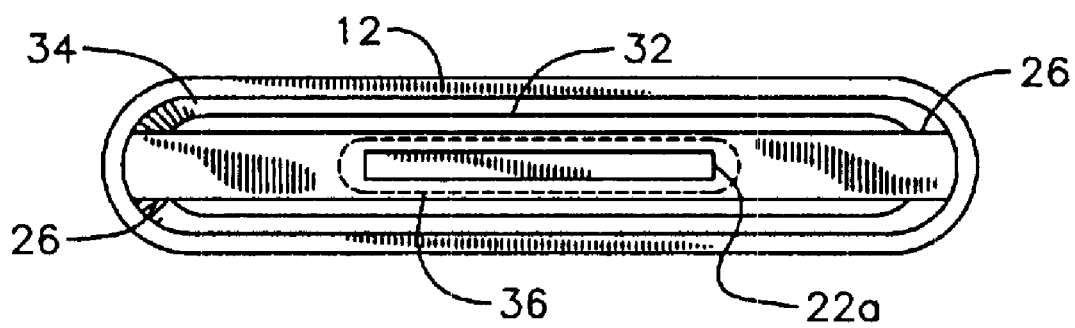
FIG. 8 is a bottom plan view of said third embodiment.
Figure 9:
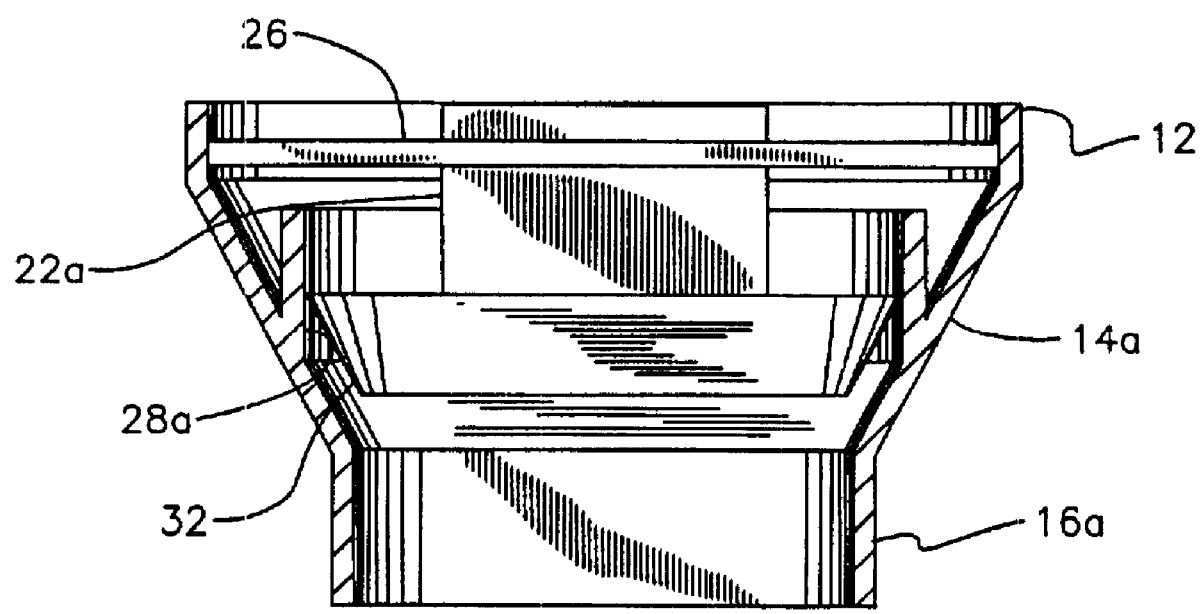
FIG. 9 is a side elevational, sectional view of an alternative embodiment of said third embodiment.

FIGS. 7 and 8 depict a third embodiment of the invention and FIG. 9 depicts a variation thereof. In the embodiment of FIGS. 7 and 8, valve body 32 is not frustoconical nor are tapered sidewalls 14a and 34. Instead, sidewalls 14a and 34 taper downwardly to form an elongate, narrow open slot 36 as depicted in FIG. 6. Valve body 32 is complementally formed so that it seats squarely against downwardly tapered sidewalls 34 when the bailer is lifted from the liquid fluid being sampled. Note that stem 22a is also narrow and elongated in this embodiment, as is downspout 16a.

The embodiment of FIG. 9 adds annular ridge 28 as in the embodiments of FIGS. 3 and 6.

This invention represents a major breakthrough in the art of bailers. Being drawn to a pioneering invention, the claims that follow are entitled, as a matter of law, to broad interpretation to protect the heart or essence of the invention from piracy.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A valve assembly for admitting liquid flow into a hollow interior of a bailer as the bailer is lowered into a liquid fluid and for retaining liquid fluid within said hollow interior when the bailer is lifted from said liquid fluid, comprising:

a support means that spans the hollow interior of said bailer;

a central bore formed in said support means, said central bore having an axis of symmetry that is substantially coincident with a longitudinal axis of symmetry of said bailer;

said bailer including frusto-conical sidewalls at a lower end thereof;

a valve means including a frusto-conical valve body secured to a lowermost end of a valve stem;

said valve stem being slideably received within said central bore so that said frusto-conical valve body rises and falls as liquid fluid flows into and out of said hollow interior of said bailer, respectively, said valve stem and said central bore cooperating to maintain said frusto-conical valve body in substantial coincidence with said longitudinal axis of symmetry of said bailer as said frusto-conical valve body rises and falls;

said frusto-conical sidewalls being configured to substantially match an exterior surface of said frusto-conical valve body so that substantially no leakage of liquid fluid from said hollow interior of said bailer occurs when said frusto-conical valve body is seated against said frusto-conical sidewalls; and an annular ridge of predetermined height integrally formed on an interior surface of said frusto-conical sidewalls, said annular ridge adapted to accommodate at least one grain of particulate matter so that said at least one grain of particulate matter does not interfere with seating of said frusto-conical valve body against said frusto-conical sidewalls.

2. The valve assembly of claim 1, wherein said support means is provided in the form of a spider means having legs that radiate outwardly relative to the longitudinal axis of said bailer.

3. The valve assembly of claim 1, wherein said annular ridges are disposed parallel to the longitudinal axis of symmetry of said bailer.

* * * * *